Figure 1:
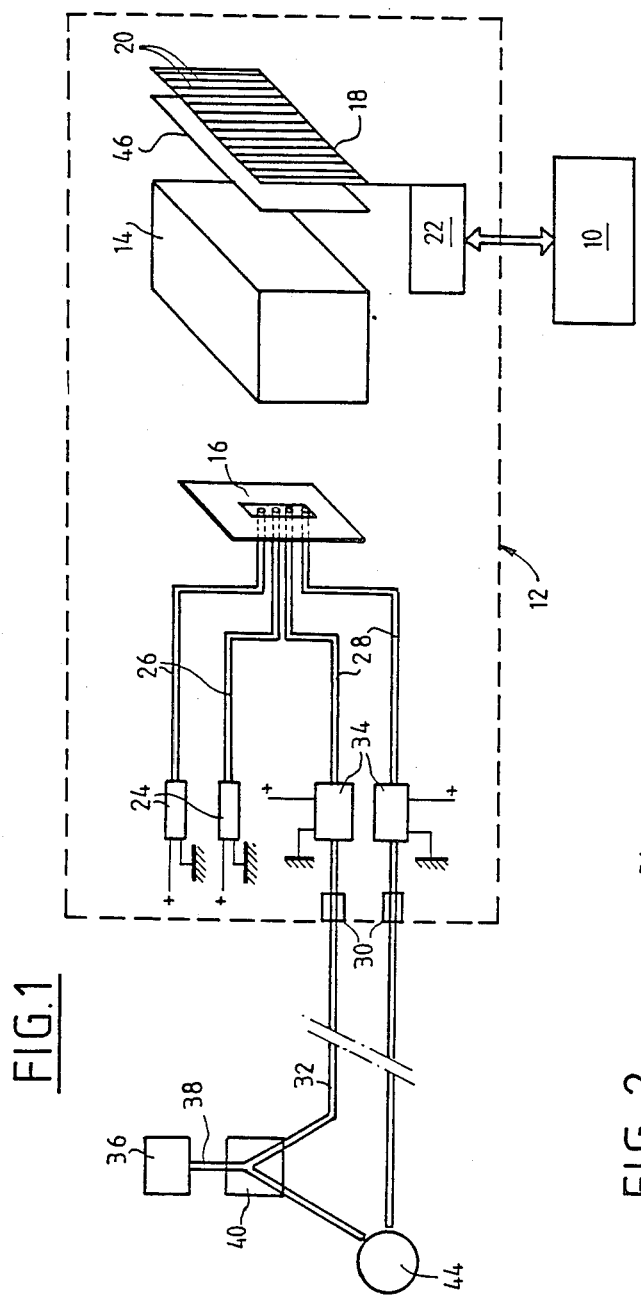

United States Patent [19]

Lequime et al.

[11] Patent Number: 4,758,085
[45] Date of Patent: Jul. 19, 1988

[54] OPTICAL FIBER SPECTROMETER/COLORIMETER APPARATUS

[75] Inventors: Michel Lequime, Eguilles; Jocelyn Millet, Pertuis; Jean Debrie, Aix en Provence, all of France

[73] Assignee: Bertin & Cie, Plaisir, France

[21] Appl. No.: 86,076

[22] PCT Filed: Oct. 14, 1986

[86] PCT No.: PCT/FR86/00351
§ 371 Date: Jun. 9, 1987
§ 102(e) Date: Jun. 9, 1987

[87] PCT Pub. No.: WO87/02454
PCT Pub. Date: Apr. 23, 1987

[30] Foreign Application Priority Data

Oct. 16, 1985 [FR] France ................. 85 15351

[51] Int. Cl.⁴ .................... G01J 3/42; G01J 3/36
[52] U.S. Cl. ........................ 356/319; 356/323; 356/328
[58] Field of Search ............... 356/319, 323, 225, 326, 356/328, 334

[56] References Cited

U.S. PATENT DOCUMENTS 3,874,799  4/1975  Isaacs et al. ............... 250/226 X

FOREIGN PATENT DOCUMENTS 2097106   3/1972  France .
2303274  10/1976  France .
57-108766  7/1982  Japan .
57-128823  8/1982  Japan .
57-73741   4/1984  Japan .
7905871    2/1981  Netherlands .
2155173    9/1985  United Kingdom .

OTHER PUBLICATIONS

Ratzlaff "Spectrophotometer Based on a CCD Photoarray Detector", Anal Chem, 1980, 52, 916-920.
Mesures, Regulation, Automatismes", vol. 49, #16, 12-84, pp. 75, 77, 79, 80.

Primary Examiner—Vincent P. McGraw
Attorney, Agent, or Firm—Dennison, Meserole, Pollack & Scheiner

[57] ABSTRACT

The invention relates to a spectrometer/colorimeter apparatus comprising an opto-electronic card (12) with the essential components of the apparatus mounted thereon, and in particular a spectrometer (14) having an inlet slot (16) and a strip (18) of photodetectors (20), and two optical fiber measurement paths (28) and two calibration paths (26), with the ends of the optical fibers being superposed in the inlet slot (16) of the spectrometer. The apparatus is particularly intended for use in an industrial environment.

16 Claims, 1 Drawing Sheet

OPTICAL FIBER SPECTROMETER/COLORIMETER APPARATUS

The invention relates to an optical fiber spectrometer/colorimeter apparatus intended, in particular, for use in an industrial environment.

Conventional good quality spectrometers and colorimeters are often apparatuses which are poorly adapted for use in an industrial environment. In general, accurate measurements can be obtained only by using them in a laboratory, with relatively long calibration operations being necessary prior to use, with samples then being taken for inspection, followed by repetitive measurements which may also take a considerable length of time depending on the amount of energy received by the spectrometer or the colorimeter, such that it is relatively difficult to associate apparatuses of this kind with continuous production lines.

The object of the present invention is a spectrometer/colorimeter apparatus capable of operating both as a spectrometer and as a colorimeter, which is presented in the form of a particularly compact integrated assembly, which is capable of performing calibration operations at regular intervals or at user request, and which is capable of performing very accurate and very rapid repetitive measurements.

To this end, the present invention provides an optical fiber spectrometer/colorimeter apparatus suitable for operating as a spectrometer and as a colorimeter, the apparatus comprising a spectrometer including an inlet and a mosaic of photodetectors, characterized in that it is essentially constituted by the association of a controlling microprocessor and an opto-electronic printed circuit card bearing the following items:

at least two optical fiber measurement paths ending at the inlet of the spectrometer, and fitted with shutters enabling the measurement paths to be switched;

wavelength calibration means for the detectors, comprising two reference emitters connected by optical fiber calibration paths to the inlet of the spectrometer;

the spectrometer and its mosaic of detectors ; and electronic circuits for reading the detectors.

An apparatus in accordance with the invention thus comprises a single assembly with the following items integrated on a single opto-electronic card: a spectrometer; spectrometer calibration means; and measuring paths which merely need extending by optical fibers to those points at which light spectrum and/or color is to be measured, which points may be at considerable distances from the apparatus.

According to another characteristic of the invention, the detectors form a strip of adequate height relative to the height of the superposed ends of the optical fibers in an inlet slot, and, for example, when the optical assembly of the spectrometer has a magnification ratio of 1/1, their height is equal to the height of said superposed optical fiber ends.

At least four measuring and calibrating paths can thus be provided without it being necessary to interconnect these paths by optical couplers upstream from the inlet slot to the spectrometer and to equip these paths with shutters, which would cause photometric losses to occur in use.

According to yet another characteristic of the invention, the width of the inlet slot is less than the core diameter of the optical fibers, thereby improving the resolution of the apparatus.

According to yet another characteristic of the invention, the measuring path shutters include electrical means for reproducing their positions, thereby making it possible to validate measurements by inspecting the positions of the shutters.

During performing measurements using a spectrometer or a colorimeter comprising a plurality of measurement paths, it is important to be able to verify that only one measurement path is open and that the others are indeed closed.

According to yet another characteristic of the invention, the above-specified measurement paths constitute independent spectrometer measurement paths when the apparatus is operating as a spectrometer, and constitute a reference path associated with a light source and at least one measurement path associated with an object illuminated by said light source when the apparatus is operating as a colorimeter.

Advantageously, this light source is associated both with the reference path and with the object to be illuminated via an optical fiber and a Y-coupler.

This improves the color measurement of the illuminated object.

According to yet another characteristic of the invention, a focal plane corrector formed by a graduated density compensation filter is disposed over the detector strip to compensate the unfavorable transmission of optical fibers in the blue region of the spectrum, and to eliminate second order diffraction from the grating.

The use of this focal plane corrector makes it possible firstly to avoid using blue filters which reduce energy flux, and secondly to guarantee than the energy flux of the various different visible spectrum lines arriving on the detectors are of the same order of magnitude.

Naturally, the type of graduated density compensation filter which is used will be a function of the lengths of the optical fibers constituting the measurement paths and of the spectrum of the light source used.

According to yet another characteristic of the invention, the electronic circuits mounted on the above-specified optoelectronic card comprise circuits for automatically adjusting the integration time of the detectors by measuring the energy flux received by the detectors, by comparing the received flux with the detector saturation threshold, and by setting the integration time so as to obtain a signal having as high a level as possible beneath said saturation threshold.

This improves the accuracy of the measurements, and the signal-to-noise ratio of spectrum and color measurements.

The circuits for automatically adjusting the detector integration time include a programmable clock under the control of the microprocessor.

Further, the means for reading the strip of detectors are of the multiplex type, with the frequency at which the detectors are read being constant and independent of the integration time.

Advantageously, in order to improve the signal-to-noise ratio, the reading frequency is adjusted as a function of the shortest integration time.

According to yet another characteristic of the invention, the circuits for processing the signals read from the detectors include an analog-to-digital converter, providing digital output on 12 bits, for example.

When the above-specified clock is programmable on 11 bits, the circuits in accordance with the invention make it possible to automatically adjust the integration time of the detectors so as to cause the signal obtained to have a value which is equal to 90% of the dynamic range of the detectors.

Further, an apparatus in accordance with the invention is also characterized in that if it includes circuits for determining the number of times the detectors should be read for a given measurement, as a function of the energy flux received by the detectors and of the corresponding integration time.

Since the integration time may vary between about one second and one millisecond as a function of the received energy flux, it is preferable for measurement speed to perform a small number of measurements when the integration time is long, and to perform a larger number of measurements when the energy flux is higher and the integration time is shorter.

The apparatus can also be used to measure detector noise by closing all of the measurement paths which may be done on a regular periodic basis or on user request, and the noise signals may be stored in a memory and subtracted from the signal measurements obtained when a measurement path is open.

This apparatus can also be used to automatically set the detectors on spectrum lines of determined wavelength, either periodically or on user request, by virtue of the calibration means provided on the opto-electronic card. In an industrial environment it may happen that the apparatus is subjected to shock, to vibration, or to thermal stresses, any which may move the strip of detectors relative to the spectromter, and although such movement is unimportant from the mechanical point of view, it can be much more important for spectrometer or colorimeter measurements.

As a result, the assembly tolerances for the apparatus itself do not need to be very tight.

Figure 2:
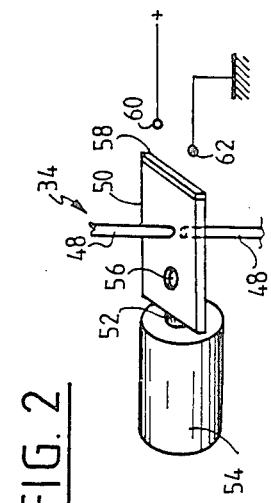

In the following description given by way of example, reference is made to the accompanying drawing, in which:

FIG. 1 is a diagrammatic view of an apparatus in accordance with the invention; and FIG. 2 is a more detailed view of a measurement path shutter of said apparatus.

Reference is made initially to FIG. 1 which is a diagram showing a spectrometer/colorimeter apparatus in accordance with the invention.

This apparatus is essentially constituted by associating a control microprocessor 10 and an opto-electronic card 12 whose outline is represented in dashed lines and on which there are mounted:

a diffraction grating type spectrometer 14, for example using a Littrow type optics comprising an inlet slot 16; and a strip 18 of photodetectors 20 which may, for example, be silicon photodiodes.

These photodetectors 20 are associated with electronic circuits given a general reference 22 which are mounted on the card 12 and which include: circuits, e.g. multiplex type circuits, for reading detector charge; and analog-to-digital converter, e.g. providing digital output on 12 bits; a programmable clock for determining the integration time of the photodetectors 20, e.g. using 11 bits; buffer memories; and circuits for processing the digitized data.

The card 12 also carries means for calibrating the photodetectors 20 in wavelength, which means are constituted in this case by two light-emitting diodes (LEDs) 24, which are optionally DC powered under the control of the microprocessor 10 and which are connected to the inlet slot 16 of the spectrometer via optical fibers 26 constituting two calibration paths. Each LED 24 emits light radiation of a given wavelength when powered, and the radiation wavelengths of the two LEDs are suitably far apart from each other in the visible spectrum.

Two optical fiber measurement paths 28 are also provided on the card 12, with one end of each measurement path being disposed at the inlet slot 16 to the spectrometer, and with the other end of each measurement path being connected via a connector 30 mounted on the card 12 to a measurement path 32 formed by an optical fiber which may be very long, if so desired.

Each measurement path 38 mounted on the card 12 is also fitted with a shutter 34 of the type shown in FIG. 2 and which is optionally DC powered under the control of the microprocessor 10 and which serves to open or close the corresponding measurement path 28.

When the apparatus is to be used as a colorimeter it is associated with a light source 36 which is constituted, for example, by a lamp emitting reference spectrum radiation, and which is connected via an optical fiber 38 and a Y-coupler 40 firstly to the input of one of the measurement paths 32 off the card 12, and secondly to an optical fiber 42 and to an object 44 to be illuminated, with the end of the other measurement path 32 of the card 12 also facing said object. The Y-coupler 40 may be provided, for example, to pass a small fraction of the energy flux which it receives at its inlet to the first measurement path 32 and to pass the remaining fraction of the flux towards the object 44.

The first measurement path 32 then constitutes a reference path for spectrometer measurement of the-light received by the object 44, while the other measurement path 32 constitutes a spectrometer measurement path for the light reflected by the object 44 and modified by the color thereof.

Preferably, in order to limit energy consumption and heat dissipation, the shutter 34 associated with the reference path is closed when in its rest position (i.e. when it is not excited), and the shutter 34 associated with the measurement path is open when in its rest position (i.e. when it is not excited), since the light reflected at 44 is, generally speaking, measured much more frequently than is the reference light emitted by the lamp 36.

When the apparatus is operating solely as a spectrometer, the measurement 32 which is not connected to the coupler 40 may be used on its own, or else, if two measurement paths to different points are desired (e.g. to an assembly line), the first measurement path 32 may be disconnected from the coupler 40 and its end may be placed at the desired location.

The number of measurement paths may be increased, if necessary by fitting them with shutters and connecting them in pairs using Y-couplers such as the coupler 40 with the common branch being connected to the inlet to a measurement path 28 on the card 12.

The ends of the optical fibers forming the measurement paths 28 and the calibration paths 26 are superposed on one another in the inlet slot 16 tot he spectrometer. The detectors 20 must therefore be of adequate height, i.e. their height must correspond to the height of the superposed ends of th optical fibers. When the spectrometer 14 used Littrow optics having a magnification ratio of 1/1, the height of the detectors 20 must be not less than the height of the superposed nds of the four optical fibers constituting the measurement and calibration paths, in other words the height must be equal to four times the diameter of a single optical fiber.

The width of the inlet slot 16 is preferably less than the diameter of the core of an optical fiber, therby increasing the resolution of the spectrometer. For example, when an optical fiber has a core diameter of about 200 microns, the width of the inlet slot 16 may be 50 microns. Naturally, a wider slot could be used, for example when more energy flux is required to perform the measurements.

As can be seen in FIG. 1, a graduated density compensation filter 46, referred to as a focal plane corrector, is placed over the photodetectors 20 so that they all receive energy flux of the same order of magnitude, and preferably so that they all receive substantially equal energy flux.

Optical fibers transmit poorly in the blue region of the spectrum, so that the energy flux of spectrum components entering the spectrometer in the blue is much less than the energy flux of the red components, and attenuation also increases with increasing length of the optical fibers constituting the measurement paths. The focal plane corrector 20 serves to reestablish substantially uniform energy flux over the photodetectors 20. Further, its use is preferable to the use of a set of blue filters which pass only a fraction of the incident energy flux.

Reference is now made to FIG. 2 which is a diagram of a shutter 34 mounted on a measurement path 28 of the card 12 of the apparatus shown in FIG. 1.

This measurement path 28 comprises two aligned optical fibers 48 whose facing ends are separated by a very narrow gap through which a small plate 50 moves perpendicularly to the optical fibers 48. The plate 50 is connected to the moving core 52 of a small electromagnet 54 which is DC powered under the control of the microprocessor 10. The plate 50 includes a hole 56 which, depending on whether the electromagnet 54 is excited or not, is moved between the ends of the optical fibers 48 or is moved away therefrom.

In the example shown, when the electromagnet 54 is not excited, the hole 56 is not opposite the ends of the fibers 48, and the reference measurement path formed by said fibers is closed. When the electromagnet 54 is excited, the hole 56 lies between the ends of the fibers 48 and the measurement or reference path is open.

The end of the plate 50 furthest from the electromagnetic 54 carries an electrically conductive trip 58 suitable for cooperating with two fixed contacts 61 and 62, one of which is connected to ground and the other of which is connected to a source of electricity so that the conductive strip 58 and the fixed contacts 60 and 62 form a switch. When the electromagnet 54 is excited, the switch is closed and electric current passes through the corresponding circuit making it possible to verify that the plate 50 has been correctly moved and that the measurement or reference path formed by the fibers 48 is open. Conversely, when the electromagnet 54 is not excited, the switch is open, thereby also making it possible to verify that the corresponding measurement or reference path is closed.

By way of concrete example, the plate 50 may be a few millimeters long, 1 to 2 mm wide, and a very thin, i.e. less than 0.1 mm thick, and it may be displaced in translation by the electromagnet 54 over a stroke of about 1 mm. The hole 56 may have a diameter of about 500 microns for fibers 48 having a core diameter of 200 microns.

The above-described apparatus operated as follows:

The operations of calibrating the photodetectors 20 may be performed automatically in a periodic manner under the control of the microprocessor 10, or else on user request. To do this, the shutters 34 on the measurement paths 28 are closed and measurements are performed by turning on one of the LEDs 24 while the other is off, and then by turning on the other LED 24 while the first is off. These measurements are repeated regularly at predetermined time intervals of given length, with the results of the first measurements being stored in memory and compared with the results of subsequent measurements, in order to verfiy that they match and to automatically recalibrate the strip of photodetectors 20, if necessary, following an accidental offset which may result, for example, from a mechanical shock, or a thermal shock, or from vibration.

In order to perform a spectrum measurement, both LEDs 24 are held off, and one of the measurement paths 28 is opened while the or each other measurement path 28 is closed. The energy flux received by the photodetectors 20 is measured and compared with the saturation threshold, in order to determine the time during which the photodetectors should integrate the received signal so as to obtain as large a signal as possible below the saturation threshold. In general, the integration time varies between about one second and one millisecond, and it is determined by an 11-bit programmable clock, thereby making it possible to automatically match the integration time to the value of the received energy flux so as to obtain a signal representing 90% of the dynamic range of the photodetectors. When the detectors are silicon photodiodes, their spectrum response band goes from 350 to 1100 nm with a dynamic range which may be as much as 5000 (ratio between the saturation threshold and the noise threshold).

Associating such detectors with a programmable clock gives the apparatus a dynamic range of $10^6$ in incident energy flux.

The signals from the detectors 20, i.e. the charges thereon, are read by multiplex type read circuits, operating at a constant read frequency equal to the maximum read frequency for the detectors of the strip, i.e. the frequency which corresponds to the minimum value of the integration time. When the photodetectors are read, the integration is reset to zero for the next measurement.

The signals read from the detectors are digitized by an analog-to-digital converter, for example a converter providing a 12-bit output singal.

It is generally desirable to make as many measurements as possible so as to improve the signal-to-noise ratio statistically by a factor proportional to the square root of n, where n is the number of measurements performed. The number n is determined as a function of the integration time for each measurement so as to ensure that the total duration of said measurements remains small, for example less than one second.

Photodetector noise is measured by closing all of the measurement paths. The measured noise is automatically subtracted from the measurement signal obtained by opening a measurement or reference path.

When the energy flux received by the photodetectors is low, and the integration time is therefore long, it may be satisfactory to perform a single measurement and then to smooth the signal obtained by mathematical transformations of the Fourier transform type. High speed software already exists which, in association with a suitable microprocessor, enables a curve to be smoothed using the Fourier transform in less than one second. It is thus faster, under such conditions when the integration time is long, to make do with a single measurement and to smooth the resulting curve using a Fourier transform, than it is to make a series of measurements which could take five to ten times as long.

When the apparatus is operating as a colorimeter, the reference path associated with the lamp 36 is opened in order to perform spectrum measurement of the radiation emitted by said lamp while the measurement path associated with the object 4 is closed; thereafter the reference path is closed while the measurement path associated with the object 44 is opened in order to perform spectrum measurement of the light reflected by said object, with the ratio of the two measurements being representative of the color of the object.

A spectrometer/colorimeter apparatus in accordance with the invention may have the following characteristics, for example:

spectrum response band=350 nm to 1100 nm;
resolving power=5 nm;
automatic wavelength calibration;
automatic compensation for mechanical misadjustment;
large dynamic range of measurable energy flux ($10^6$);
automatic adjustment of detector integration time making use of 90% of detector dynamic range;
use of an opto-electronic card of standard 100 nm width bearing a spectrometer housed in a rectangular box having dimensions of about 95 mm×35 mm×40 mm, with integrated measurement, calibration, and processing subassemblies.

We claim:

1. An optical fiber spectrometer/colorimeter apparatus suitable for operating as a spectrometer and as a colorimeter, the apparatus comprising a spectrometer (14) including an inlet (16) and a mosaic of photodetectors (20), characterized in that it is essentially constituted by the association of a controlling microprocessor (10) and an opto-electronic printed circuit card (12) bearing the following items:

at least two optical fiber measurement paths (28) ending at the inlet (16) of the spectrometer, and fitted with shutters (34) enabling the measurement paths to be switched ;
wavelength calibration means for the detectors (20), comprising two reference emitters (24) connected by optical fiber calibration paths (26) to the inlet (16) of the spectrometer ;
the spectrometer (14) including the mosaic of detectors (20) ; and
electronic circuits (22) for reading the detectors (20).

2. Apparatus according to claim 1, characterized in that the detectors (20) form a strip (18) of adequate height relative to the height of the ends of the optical fibers superposed in an inlet slot (16), which height is, for example, equal to the height of the superposed optical fiber ends.

3. Apparatus according to claim 2, characterized in that the width of the inlet slot (16) is less than the core diameter of the optical fibers.

4. Apparatus according to claim 1, characterized in that the shutters (34) on the measurement paths include electrical means (58, 60, 62) for reproducing their positions, thereby making it possible to validate measurements by verifying the positions of the shutters.

5. Apparatus according to claim 1, characterized in that the measurement paths (28, 32) constitute independent spectrometric measurement paths when the apparatus operates as a spectrometer, and constitute a reference path associated with a light source (36) and at least one measurement path associated with an object (44) illuminated by said source when the apparatus operates as a colorimeter.

6. Apparatus according to claim 5, characterized in that the light source (36) is associated firstly with a reference path (32) and secondly with an object (44) to be illuminated by optical fiber means (38) and a Y-coupler (40).

7. Apparatus according to claim 5, characterized in that the shutter (34) associated with the reference path is closed at rest, whereas as the shutter (34) associated with a measurement path is open at rest.

8. Apparatus according to claim 2, characterized in that a focal plane corrector (46) formed by a graduated density compensation filter is disposed over the strip (18) of detectors (20) in order to compensate for the poor transmission of optical fibers in the blue region of the spectrum.

9. Apparatus according to claim 1, characterized in that the reference emitters associated with the calibration paths (26) are light-emitting diodes (24) emitting predetermined different spectrum bands in the visible spectrum.

10. Apparatus according to claim 1, characterized in that the circuits (22) mounted on the opto-electronic card (12) include circuits for automatically adjusting the detector integration time: by measuring the energy flux received by the detectors; by comparing the received flux with the saturation threshold of the detectors; and by setting the integration time so as to obtain a signal whose level is as high as possible below said saturation threshold.

11. Apparatus according to claim 10, characterized in that the circuits for automatically adjusting the integration time of the detectors include a programmable clock controlled by the microprocessor (10).

12. Apparatus according to claim 1, characterized in that the circuits for measuring the detector sgnals are also suitable for measuring the noise signals from the detectors (20) when the shutters (34) of the measurement paths are closed, circuits being provided to subtract said noise signals from measurement signals as obtained when a measurement path shutter (34) is open.

13. Apparatus according to claim 1, characterized in that the circuit for reading the detectors (20) are of the multiplex type, with the detector reading frequency being constant and independent of the integration time, and equal, for example, to the maximum frequency for reading the detectors (20) corresponding to the shortest integration time.

14. Apparatus according to claim 1, characterized in that the circuits for processing the information read include an analog-to-digital converter, providing an output signal on 12 bits, for example.

15. Apparatus according to claim 1, characterized in that the microprocessor includes means for determining the number of times the detectors are to be read for performing a given measurement as a fucntion of the value of the energy flux received by the detectors (20).

16. Apparatus according to claim 15, characterized in that the microprocessor performs Fourier transform smoothing when the number of reads is small.

* * * * *